(12) United States Patent
Roorda

(10) Patent No.: US 6,283,949 B1
(45) Date of Patent: Sep. 4, 2001

(54) REFILLABLE IMPLANTABLE DRUG DELIVERY PUMP

(75) Inventor: Wouter Erik Roorda, Palo Alto, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/472,656

(22) Filed: Dec. 27, 1999

(51) Int. Cl.[7] .................................................. A61M 1/00
(52) U.S. Cl. ............................. 604/288.02; 604/288.04; 604/153; 128/DIG. 12
(58) Field of Search ........................... 417/477.7, 477.11; 604/891.1, 890.1, 132, 133, 151, 153, 154, 288.01–288.04, 257; 128/DIG. 12, DIG. 13

(56) References Cited

U.S. PATENT DOCUMENTS

| | | | |
|---|---|---|---|
| 4,013,074 | 3/1977 | Siposs | 604/891.1 |
| 4,210,138 | 7/1980 | Jess et al. | 64/67 |
| 4,692,147 | 9/1987 | Duggan | 604/891.1 |
| 4,931,050 | 6/1990 | Idriss | 604/891.1 |
| 5,061,242 | 10/1991 | Sampson | 604/118 |
| 5,207,666 | 5/1993 | Idriss et al. | 604/891.1 |
| 5,443,459 | 8/1995 | Wong et al. | 604/892.1 |
| 5,498,255 | 3/1996 | Wong | 604/892.1 |
| 5,531,736 | 7/1996 | Wong et al. | 604/892.1 |
| 5,752,930 | 5/1998 | Rise et al. | 604/891.1 X |
| 5,820,589 | 10/1998 | Torgerson et al. | 604/93.01 |
| 5,836,935 | 11/1998 | Ashton et al. | 604/891.1 |
| 5,843,069 | 12/1998 | Butler et al. | 604/891.1 |
| 5,976,109 | 11/1999 | Heruth | 604/140 |

OTHER PUBLICATIONS

"There Is Only One Port–A–Cath®. . . ", Port–A–Cath® Implantable Access Systems, SIMS Deltec, Inc. (1996).

"The Power of Two Materials in One Portal", Port–A–Cath® II Implantable Access Systems, SIMS Deltec, Inc. (1996).

"Phase I/II Clinical Study Results of Duros™ Leuprolide Implant for Prostate Cancer Treatment Announced at AUA Meeting", downloaded Dec. 20, 1999 from <http:www.alza-.com/pr/PR374.htm> (Initial publication date listed as Jun. 4, 1998).

"Intraspinal Drug Delivery Pumps", downloaded Dec. 20, 1999 from <http://www.asri.edu/neuro/brochure/pain6.htm>, Allegheny–Singer Research Institute (Last Updated: Feb. 21, 1998).

Gabriel Spera, "Implantable Pumps Improve Drug Delivery, Strengthen Weak Hearts", downloaded Dec. 20, 1999 from <http://www.devicelink.com/mddi/archive/97/09/013.html> (1997).

(List continued on next page.)

Primary Examiner—Anhtuan T. Nguyen
(74) Attorney, Agent, or Firm—Skjerven Morrill Macpherson; Peter H. Kang

(57) ABSTRACT

An implantable drug delivery pump includes a reservoir, a dispensing chamber adjacent to the reservoir, a dispensing passage provided along an interior surface of the dispensing chamber, and an actuator for applying a moving compressive force onto the dispensing passage. The pump is subcutaneously implantable in a patient, and a drug is injected into the reservoir through a septum provided on a housing for the reservoir. As the compressive force applied by the actuator moves along the dispensing passage, the drug preparation is simultaneously pushed out of the dispensing passage into a catheter for delivery to the desired site, and additional drug preparation is drawn into the dispensing passage from the reservoir. The actuator includes a rotating arm driven by an motor at a controllable rate.

30 Claims, 1 Drawing Sheet

OTHER PUBLICATIONS

"About Advanced Pain Therapies (APT)", downloaded Dec. 20, 1999 from <http://www.medtronic.com/neuro/apt/about3.html>, Medtronic, Inc. (1999).

"Pump: Internal Views of Component Parts", downloaded Dec. 20, 1999 from <http://www.southshoreneurlogic.com/itb/itb–manage–pump.html> (Initial publication date unknown).

"SynchroMed E1 Infusion System: SynchroMed Pump Enhancements", downloaded Dec. 20, 1999 from <http://www.southshoreneurologic.com/itb/itb–synchromed el.html> (Initial publication date unknown).

"Schematic—Pictorial of ITB pump and placement" downloaded Dec. 20, 1999 from <http://www.southshoreneurologic.com/itb/itb–hospital5.html> (Initial publication date unknown).

REFILLABLE IMPLANTABLE DRUG DELIVERY PUMP

BACKGROUND

1. Field of the Invention

This invention relates to drug delivery devices and more specifically to implantable devices for delivering drugs.

2. Description of Related Art

Localized drug delivery has become increasingly important in applications such as tissue engineering, growth regulation, pain control, and therapeutic approaches to localized disease conditions including tumors, local nervous system conditions, and local vascular system conditions. The action of many drugs is greatly enhanced by, or in some cases requires, long-term local delivery of those drugs into the patient's body.

One method of localized drug delivery is injection of the drug at a local site at which the drug acts. Localized drug delivery may be combined with a slow release drug formulation. Disadvantages of localized drug injection include the difficulty of stabilizing the drug over the total release period and adequately controlling the concentration profile of the drug over time at the site of action during delivery.

Another method for localized drug delivery includes inserting a catheter to direct the drug to the desired body site, and using a pump to impel a drug through the catheter. An externally worn pump is conventionally used with an internally implanted catheter. However, the site of entry into the patient's body is prone to infection. In addition, the externally worn pump is bulky and inconvenient.

Implantable drug delivery devices, implantable pumps, for example, have been developed to address the disadvantages of techniques that use external pump and catheter systems. Implantable drug delivery pumps often include a reservoir for storing the drug, an injection port to enable injection of fresh drug preparations at regular intervals into the reservoir, and optionally a catheter for delivering the drug to the desired site. Application of fresh drug preparations avoids a problem of long term stabilization. One disadvantage of implantable drug delivery devices is an inherent difficulty in controlling the dosage and delivery rates from the reservoir through the catheter. A further problem is that many of the applications for implantable drug delivery utilize drugs that are not stable at body temperature for extended periods.

An implantable device known as the Duros implant, which is manufactured and sold by Alza Corporation, Mountain View, Calif., provides drug treatment by osmotically delivering the drug preparation into the patient. Osmotic delivery uses neither mechanical or electronic assistance so that the Duros implant device can be made very small, about the size of a few matchsticks. However, the Duros implant does not permit an easily adjustable delivery rate, cannot be refilled, and requires surgical implantation. In addition, the Duros implant has only a very small reservoir for storing the drug preparation.

The limited capacity reservoir may not be a significant problem for short-term delivery of drugs, but many patients are unwilling to undergo surgical implantation for only a short-term benefit. To use the limited capacity reservoir for long-term drug delivery, a concentrated, potent drug preparation must be delivered in small dosages over an extended delivery period, resulting in problems of long-term drug instability and low precision in dosage control.

Another type of implantable drug delivery device is an infusion pump, such as a SynchroMed Infusion System which is manufactured and sold by Medtronic, Inc., Minneapolis. The device includes a catheter and a pump section. The pump section further includes a collapsible reservoir and a fill port for refilling the reservoir with fresh drug preparation. SynchroMed automatically delivers a controlled amount of medication through the catheter using an electronically driven pump. The dosage, rate, and timing are programmed into electronics contained within the pump section from an external programming device. The external programmer transmits programming information using radio waves.

SynchroMed solves some long-term delivery and dosage accuracy problems of other devices, but the pump section is large and bulky, measuring approximately 8.5 cm in diameter and 2.5 cm in height, and weighing about 205 g. The size of the SynchroMed limits the flexibility of doctors in implanting the device. Because of the large size and awkward hockey-puck shape, the SynchroMed device must typically be implanted in the abdominal cavity of a patient, and an extended catheter is passed through the patient's body to deliver the drug to the desired site of administration. In addition to problems with size and placement, the SynchroMed device is burdened by complex electronics for both programming and pumping functionality.

SUMMARY

In accordance with various aspects of the invention, an implantable drug delivery device includes a dispensing chamber having an upper surface, the dispensing chamber comprising a dispensing passage having an intake end and an outlet end, and an actuator for applying a compressive force on the dispensing passage moving in a direction from the intake end towards the outlet end. A reservoir housing is provided adjacent the upper surface of the dispensing chamber, and a reservoir in fluid communication with the intake end of the dispensing passage is provided in the reservoir housing. One-way intake valves at the intake and outlet ends of the dispensing passage ensure proper one-way flow of the drug preparation through the device.

In one aspect, the dispensing passage is a flexible tube along an interior portion of a dispensing chamber. An arm inside the dispensing chamber imposes a moving compressive force on the dispensing passage, thereby urging the drug preparation out of the outlet end and drawing additional drug preparation from the reservoir into the dispensing passage. Additional drug preparation can be injected into the reservoir through a septum on the device's housing.

In accordance with another aspect, a method for operating an implantable drug delivery device includes providing a dispensing chamber having an upper surface, an interior surface, and an outer circumferential surface, providing a dispensing passage along an interior surface of the dispensing chamber, and providing a reservoir filled with a fluid and in fluid communication with an intake end of the dispensing passage. The reservoir is housed in a reservoir housing adjacent to the upper surface of the dispensing chamber and having an outer circumferential surface concentric with the outer circumferential surface of the dispensing chamber. A compressive force is applied on the dispensing passage, and the compressive force is moved in a direction from the intake end towards an outlet end, thereby urging fluid contained between the compressive force and the outlet end out of the outlet end, and drawing fluid from the reservoir into the dispensing passage through the intake end.

BRIEF DESCRIPTION OF THE DRAWINGS

Use of the same reference symbols in different figures indicates similar or identical items.

DETAILED DESCRIPTION

Figure 1:
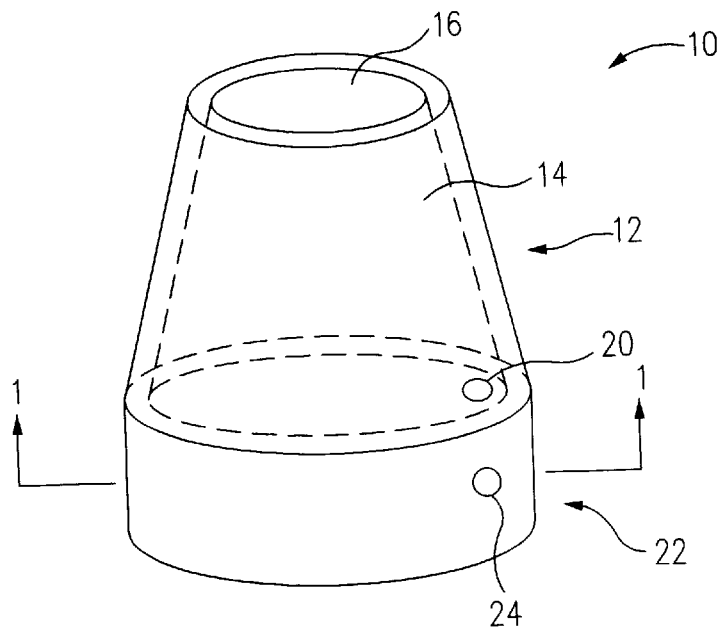
FIG. 1 shows an isometric view of an implantable drug delivery device in accordance with an aspect of the present invention.

An implantable drug delivery device 10 is shown in FIG. 1, including a reservoir housing 12, which serves as a housing for a reservoir 14. Reservoir housing 12 is made of a bio-compatible, implantable material of sufficient strength to operate without damage. For example, the housing may be constructed from a metal, such as titanium, nickel titanium, stainless steel, anodized aluminum, or tantalum, or a plastic, such as polyethylene, nylon, or polyurethane. Alternatively, a composite or ceramic may also be used. Reservoir housing 12 includes a filling septum 16, which enables a physician to inject drugs into reservoir 14 after device 10 is implanted under a patient's skin. Reservoir 14 may be made of a drugcompatible material, such as silicone, polyurethane, polyacrylate, polymethacrylate, or polyethylene, which allows reservoir 14 to expand or collapse as fluid is added or withdrawn. An elastic material may be used for this purpose. In one embodiment, reservoir 14 has a capacity of up to ten ml of drugs for extended delivery.

Reservoir 14 is in fluid connection with a first end of a dispensing passage 18 through a one-way intake valve 20. Dispensing passage 18 is a flexible tube provided along an inner surface of a solid dispensing chamber 22. In one embodiment, dispensing passage 18 is a cylindrical tube constructed of the same material from which reservoir 14 is formed. Alternatively, dispensing passage 18 is a wide, flat tube along the inner cylindrical surface of dispensing chamber 22.

Figure 2:
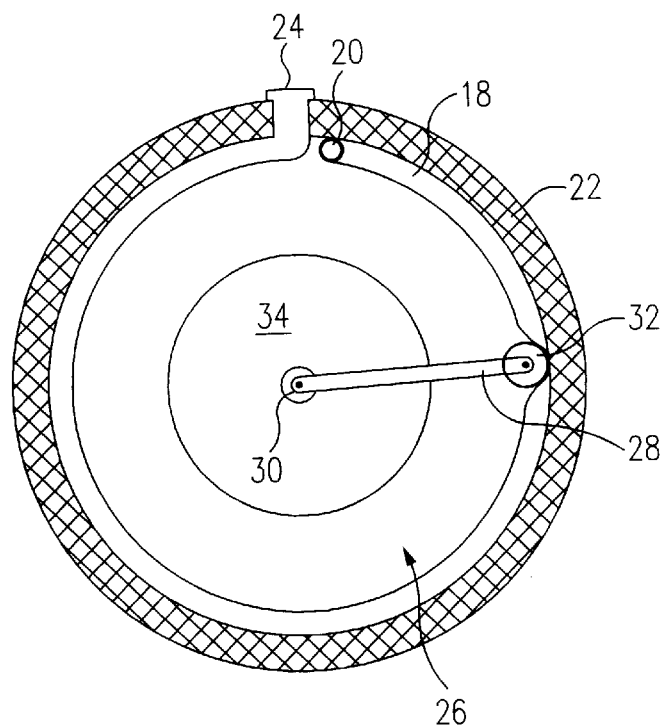
FIG. 2 is a cross-sectional view of the device in FIG. 1 taken along line 1—1.

An outlet valve 24 is formed at a second end of dispensing passage 18. Outlet valve 24 is connected to a catheter (not shown), which is used to carry the drug to the desired location in the patient's body. In the embodiment illustrated in FIGS. 1 and 2, outlet valve 24 is connected to a side of dispensing chamber 22. Alternatively, outlet valve 24 may be located anywhere, such as on the underside of device 10, opposite intake valve 20. In the embodiment shown in FIG. 2, dispensing passage 18 is mounted along substantially the entire circumference of the inner surface of dispensing chamber 22.

An actuator 26 is enclosed within the interior of dispensing chamber 22 and is capable of applying a compressive force on the dispensing passage 18. Actuator 26 includes a rotating compressor (shown in FIG. 2 as a rotating arm 28) that is rotatable about an axis 30 at the center of circular dispensing chamber 22. A contact member 32 is connected at an end of rotating arm 28 and makes compressive contact with dispensing passage 18. In one embodiment, contact member 32 is a cylindrical roller that is sufficiently wide to apply pressure across the width of dispensing passage 18. The contact member 32 is positioned so that the compressive force applied by member 32 separates the portion of drug preparation in dispensing passage 18 on an outlet side of the member 32 between member 32 and outlet valve 24 from the portion on an inlet side of the member 32 between member 32 and inlet valve 18. In another embodiment, device 10 may have a plurality of arms 28 and contact members 32, positioned at multiple points along the length of dispensing passage 18.

In one embodiment, drive system 34 includes a tiny electric motor and a battery, and can be programmed to rotate arm 28 at an adjustable speed if desired for a particular application. Alternatively, the motor in drive system 34 rotates arm 28 at a constant speed, simplifying the operation of drive system 34. In a basic embodiment, drive system 34 can be constructed from the same, readily-available mechanical components as a simple watch. In yet another embodiment, a spring, compressed gas, or osmotic engine is used to mechanically drive the actuator.

By locating reservoir housing 12 adjacent to the upper surface of dispensing chamber 22, implantable device 10 advantageously achieves an extremely small footprint. In the embodiment shown in FIGS. 1–2, the outer circumferential surface of reservoir housing 12 is roughly the same size and concentric with the outer circumferential surface of dispensing chamber 22. The outer circumferential surfaces define the footprints of dispensing chamber 22 and reservoir housing 12. Thus, in the embodiment shown, the footprints of dispensing chamber 22 and reservoir housing 12 are approximately equal. Thus, the footprint of device 10 is therefore dictated by the circumference of the dispensing chamber 22. An increase in drug reservoir size affects only the height, but not the width (i.e., footprint), of the overall device 10.

Device 10 can be subcutaneously implanted into a patient's body, and the catheter can be led intravenously or via an extravascular tunneling technique to the site where the drug is delivered. Device 10 is located such that septum 16 is readily accessible, enabling injection of a fresh drug preparation into deformable reservoir 14. A small size allows device 10 to be implanted very close to the desired site of administration without tunneling an extended catheter through the patient's body. Device 10 provides a controlled, adjustable, and refillable mechanism for delivering drugs and formulation to the patient. Device 10 therefore advantageously provides an implantable drug delivery device having the utility of larger existing delivery devices while attaining a significantly smaller size than the SynchroMed device, thereby facilitating more convenient and direct implantation. Device 10 provides a much more controllable and versatile method for drug delivery than the Duros.

Unlike other devices that immediately begin uncontrolled delivery of the drug through a catheter, device 10 delivers the drug at a controlled rate determined by the speed of rotation of arm 28. As arm 28 rotates, contact member 32 generates a moving compressive force along the length of dispensing passage 18. As contact member 32 travels along dispensing passage 18, the drug contained in the portion of dispensing passage 18 on the outlet side of contact member 32 is urged out of outlet valve 24 and into the catheter for delivery into the patient's body. At the same time, the portion of dispensing passage 18 immediately on the inlet side of member 32 is no longer compressed by member 32 and recoils to regain the original shape, thereby drawing fluid from reservoir 14 through intake valve 20 to refill dispensing passage 18.

As contact member 32 reaches the end of dispensing passage 18 at the location of outlet valve 24, contact member 32 continues rotating past the outlet valve 24 and the intake valve 20 to restart the delivery process. The drugs contained in reservoir 14 are continuously delivered through a catheter into the patient's body at a precisely controlled rate which is determined by the speed of rotating arm 28. Arm 28 continuously rotates in one direction so that very simple mechanics can be used for rotating arm 28.

In another embodiment, the compressive force applied to dispensing passage 18 can be repetitively applied along a limited portion of dispensing passage 18 rather than applied along the circular path as described above. In yet another embodiment, multiple compressive forces can be applied along the length of dispensing passage 18 to create a flow of a drug preparation through passage 18.

To assist the flow of fluid from reservoir 14 into dispensing passage 18, a material is provided between reservoir 14 and reservoir housing 12. This material can be a liquid at low temperatures, but a vapor at body temperature. Thus, prior to implantation, the pressure-providing material is in liquid form, applying only a minimal compressive force onto reservoir 14. After implantation, the material vaporizes, expanding in volume and creating an increased compressive force onto reservoir 14, which assists the flow of fluid into dispensing passage 18. One exemplary material is a compound of fluorine, carbon, and possibly chlorine, and is sold under the trade name Freon. Alternatively, the material can be a compressed gas. Reservoir housing 12 should be hermetically sealed to prevent leakage of the pressure-providing material.

When used with a stable drug preparation, device 10 can be used as a long-term drug delivery device in which reservoir 14 is filled with a large quantity of the drug preparation which is accurately delivered to the desired site in controlled amounts. Alternatively, device 10 is easily refillable and may otherwise be used with a relatively unstable drug that is frequently injected through septum 16 to refill reservoir 14.

In the case of short-term delivery, the drug preparation can be delivered at a precisely controlled rate. Device 10 utilizes relatively simple mechanical components and is simple to manufacture, reliable, and fits within a small housing. In one embodiment, device 10 measures approximately 1" in height and has a footprint diameter of about one inch. The dimensions are variable and depend largely on the desired capacity of reservoir 14. The device 10 attains a controlled delivery using an implantable refillable reservoir that is compact and unobtrusive when implanted in the patient's body.

Although the invention has been described with reference to particular embodiments, the description is only an example of the invention's application and should not be taken as a limitation. In particular, even though much of preceding discussion is directed to a cylindrical dispensing chamber 22 with a rotating arm 28, the dispensing chamber 22 can alternatively be constructed in any suitable shape and the compressive force onto dispensing passage 18 can be applied using alternative mechanical components. Various other adaptations and combinations of features of the embodiments disclosed are within the scope of the invention as defined by the following claims.

I claim:

1. An implantable drug delivery device, comprising:
    a dispensing chamber having an upper surface, said dispensing chamber comprising:
        a dispensing passage formed along an interior surface of said dispensing chamber and having an intake end and an outlet end; and
        an actuator for applying to said dispensing passage a rotational compressive force moving in a direction from said intake end towards said outlet end; and
    a reservoir housing provided adjacent said upper surface of said dispensing chamber and having a reservoir provided therein, said reservoir being in fluid communication with said intake end of said dispensing passage; and
    means for filling said reservoir, wherein said means for filling is provided in relation to a surface of said reservoir housing which is not adjacent to said upper surface of said dispensing chamber.

2. The device of claim 1, wherein said reservoir housing has a footprint size approximately equal to an outer circumferential size of said dispensing chamber.

3. The device of claim 2, wherein said reservoir housing has a circular outer surface and said dispensing chamber has a circular outer surface coaxial with said circular outer surface of said reservoir housing.

4. The device of claim 1, further comprising a one-way intake valve formed at said intake end.

5. The device of claim 1, further comprising a one-way outlet valve formed at said outlet end.

6. The device of claim 1, wherein said actuator generates a plurality of compressive forces on said dispensing passage.

7. The device of claim 1, wherein said dispensing passage is a flexible tube.

8. The device of claim 1, further comprising a material provided between said reservoir and said reservoir housing to apply a compressive force onto said reservoir.

9. The device of claim 8, wherein said material is a liquid at low temperature and vaporizes at body temperature.

10. The device of claim 1, wherein said means for fill said reservoir includes a septum for filling said reservoir with fluid.

11. The device of claim 1, further comprising a catheter attached to said outlet end of said dispensing passage.

12. The device of claim 1, wherein said actuator applies said compressive force to compress said dispensing passage between said actuator and said interior portion of said dispensing chamber.

13. An implantable drug delivery device comprising:
    a dispensing chamber having an upper surface, said dispensing chamber comprising:
        a dispensing passage formed along an interior surface of said dispensing chamber and having an intake end and an outlet end, wherein said interior surface of said dispensing chamber is circular, whereby said dispensing passage is provided on a circular path along said interior surface; and
        an actuator for applying to said dispensing passage a compressive force moving in a direction from said intake end towards said outlet end, said actuator comprising:
            a rotatable compressor having an axis of rotation at a center of the circular path of said dispensing passage;
            a contact member connected on an end of said rotatable compressor distal from said axis of rotation, said contact member generating said compressive force on said dispensing passage; and
            a motor for rotating said rotatable compressor; and
    a reservoir housing provided adjacent said upper surface of said dispensing chamber and having a reservoir provided therein, said reservoir being in fluid communication with said intake end of said dispensing passage.

14. The device of claim 13, wherein said contact member comprises a roller.

15. The device of claim 13, wherein said actuator further comprises a battery for generating power to said motor.

16. The device of claim 13, wherein said motor rotates said rotatable compressor at an adjustable rate.

17. The device of claim 13, wherein said dispensing passage is provided along said interior surface of said dispensing chamber such that said intake end is adjacent said outlet end.

18. A method for operating an implantable drug delivery device, comprising:

providing a dispensing chamber having an upper surface, an interior surface, and an outer circumferential surface;

providing a dispensing passage along an interior surface of a dispensing chamber, said dispensing passage having an intake end and an outlet end;

providing a reservoir filled with a fluid and in fluid communication with said intake end of said dispensing passage;

housing said reservoir in a reservoir housing adjacent to said upper surface of said dispensing chamber and having an outer circumferential surface concentric with said outer circumferential surface of said dispensing chamber;

applying a compressive force on said dispensing passage; and moving said compressive force in a direction from said intake end towards said outlet end, thereby urging fluid contained between said compressive force and said outlet end out of said outlet end, and drawing fluid from said reservoir into said dispensing passage through said intake end.

19. The method of claim 18, further comprising injecting fluid into said reservoir.

20. The method of claim 18, wherein:

said providing said dispensing passage comprises providing said dispensing passage such that said dispensing passage traces a circular path along said interior portion of said dispensing chamber;

said applying said compressive force comprises providing a rotatable compressor having a contact member at one end, said compressor compressing said dispensing passage between said contact member and said interior portion of said dispensing chamber; and said moving said compressive force comprises rotating said compressor about an axis of rotation at a center of said circular path, thereby moving said contact member along said dispensing passage in a direction from said intake end towards said outlet end.

21. The method of claim 18, further comprising inserting a material between said reservoir and said reservoir housing to apply a compressive force onto said reservoir.

22. The device of claim 21, wherein inserting said material between said reservoir and said reservoir housing comprises inserting a material which is a liquid at low temperature and a gas at body temperature.

23. An implantable drug delivery device, comprising:

a dispensing chamber having an upper surface, a round inner surface, and a round outer surface;

a reservoir adjacent to said upper surface of said dispensing chamber and having a round outer surface concentric with said round outer surface of said dispensing chamber;

a dispensing passage provided along a circular path on said round inner surface of said dispensing chamber, said dispensing passage having an intake end connected to said reservoir and an outlet end adjacent said intake end;

a rotatable arm rotatable about an axis of rotation located at a center of said circular path;

a contact member provided on an end of said rotatable arm distal to said axis of rotation, said contact member compressing said dispensing passage against said inner surface of said dispensing chamber; and a motor for rotating said rotatable arm.

24. The device of claim 23, further comprising a catheter attached to aid outlet end.

25. The device of claim 23, further comprising a one-way intake valve provided at said intake end.

26. The device of claim 23, further comprising a one-way outlet valve provided at said outlet end.

27. An implantable drug delivery device, comprising:

a dispensing chamber having an upper surface, said dispensing chamber comprising:

a dispensing passage formed along an interior surface of said dispensing chamber and having an intake end and an outlet end; and an actuator for applying to said dispensing passage a rotational compressive force moving in a direction from said intake end towards said outlet end; and a reservoir housing provided adjacent said upper surface of said dispensing chamber and having a reservoir provided therein, said reservoir being in fluid communication with said intake end of said dispensing passage; and a filling septum provided in relation to a surface of said reservoir housing which is not adjacent to said upper surface of said dispensing chamber.

28. The device of claim 27, wherein said reservoir housing has a footprint size approximately equal to an outer circumferential size of said dispensing chamber.

29. The device of claim 27, further comprising a material provided between said reservoir and said reservoir housing to apply a compressive force onto said reservoir.

30. The device of claim 27, wherein said dispensing passage is provided along said interior surface of said dispensing chamber such that said intake end is adjacent said outlet end.

* * * * *

UNITED STATES PATENT AND TRADEMARK OFFICE
CERTIFICATE OF CORRECTION

PATENT NO. : 6,283,949 B1
DATED : September 4, 2001
INVENTOR(S) : Wouter Erik Roorda It is certified that error appears in the above-identified patent and that said Letters Patent is hereby corrected as shown below:

Column 6,
Line 23, change "fill" to -- filling --.

Column 8,
Line 18, change "aid" to -- said --.

Signed and Sealed this

Fourteenth Day of January, 2003

JAMES E. ROGAN
*Director of the United States Patent and Trademark Office*